United States Patent [19]

Niznick

[11] Patent Number: 4,488,875
[45] Date of Patent: Dec. 18, 1984

[54] CONNECTOR FOR OVERDENTURE

[75] Inventor: Gerald A. Niznick, Encino, Calif.

[73] Assignee: A&L Investment Company, Encino, Calif.

[21] Appl. No.: 540,124

[22] Filed: Oct. 7, 1983

Related U.S. Application Data

[62] Division of Ser. No. 372,945, Apr. 29, 1982, Pat. No. 4,431,416.

[51] Int. Cl.³ .............................................. A61C 8/00
[52] U.S. Cl. .................................... 433/173; 433/177
[58] Field of Search ............... 433/173, 174, 175, 176, 433/177

[56] References Cited

U.S. PATENT DOCUMENTS

| 711,324 | 10/1902 | Lacy | 433/173 |
| 866,304 | 9/1907 | Roach | 433/177 |
| 4,359,318 | 11/1982 | Gittleman | 433/173 |

Primary Examiner—Robert Peshock
Attorney, Agent, or Firm—Flam & Flam

[57] ABSTRACT

A pillar attached directly or indirectly to the jawbone, has an accessible snap-in ball socket. A ball attached to and projecting from an overdenture or other removable prosthesis is sized to enter the socket after being forced through its restricted opening. The overdenture is fitted in such manner that in the absence of occlusal forces, the ball lies at or just inwardly of the restriction. The socket is extended inwardly so that, upon the application of occlusal forces, the ball moves deeper into the socket without imposing stress upon the pillar or its supporting structure. Yet lateral stability is provided.

2 Claims, 6 Drawing Figures

U.S. Patent  Dec. 18, 1984  4,488,875
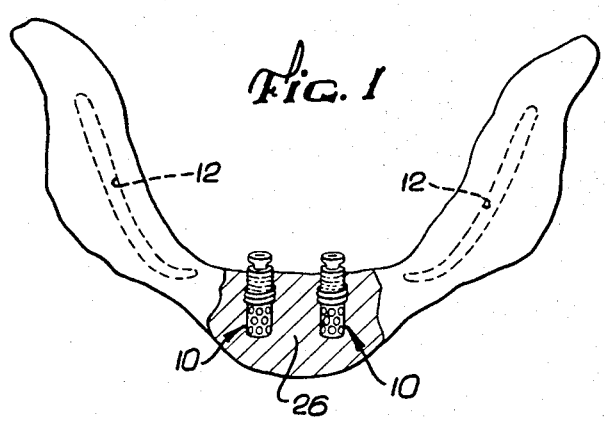
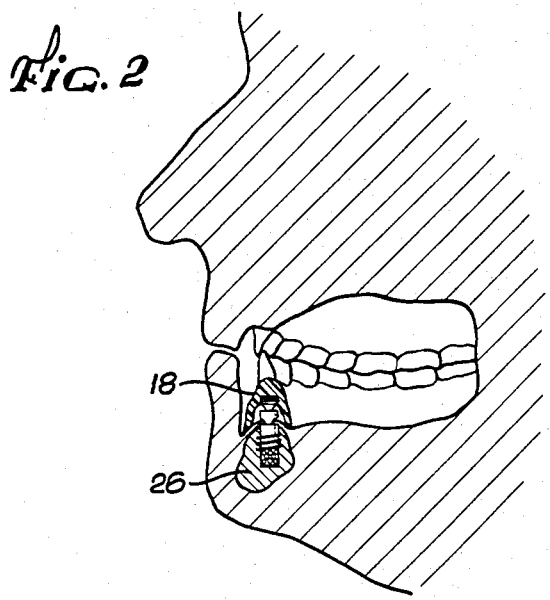
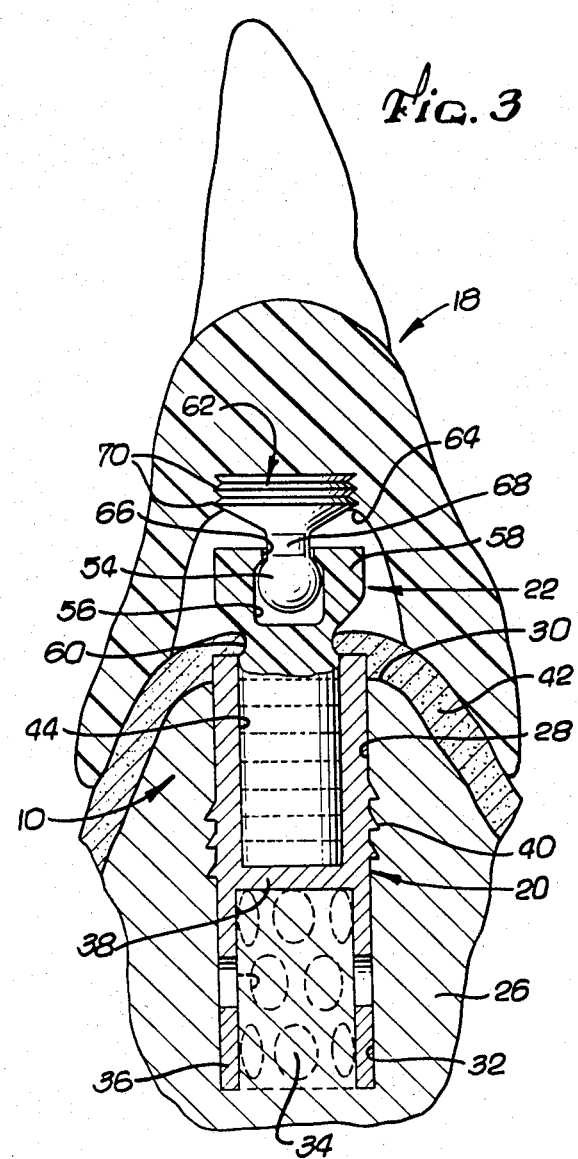
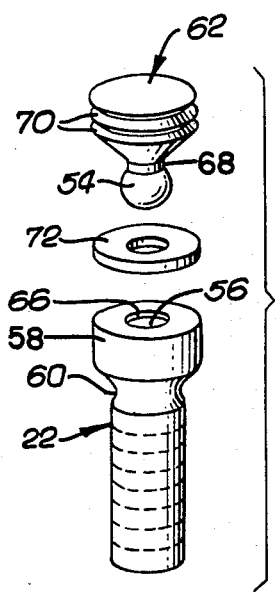
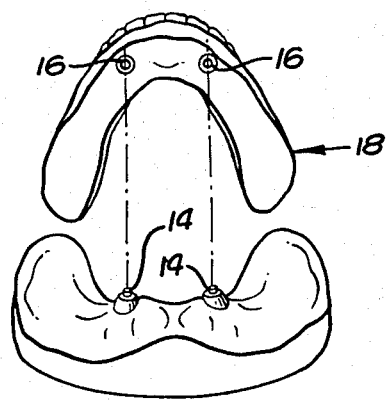
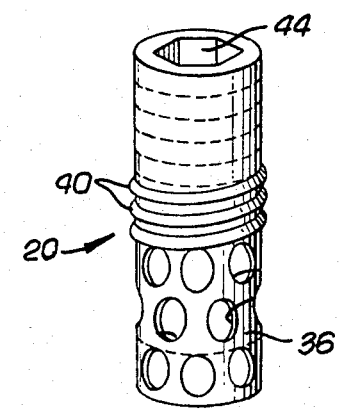

CONNECTOR FOR OVERDENTURE

RELATED APPLICATIONS

This application is a division of Ser. No. 372,945 filed Apr. 29, 1982 entitled ENDOSSEOUS DENTAL IMPLANT SYSTEM FOR OVERDENTURE RETENTION, CROWN AND BRIDGE SUPPORT, now U.S. Pat. No. 4,431,416, issued Feb. 14, 1984.

FIELD OF INVENTION

This invention relates to attachments for stabilizing overdentures or other removable prostheses.

BACKGROUND OF THE INVENTION

A variety of two part attachments have been provided for stabilizing an overdenture. Known devices, while achieving a stabilizing function, unnecessarily impose stresses on the attachment parts, on the tooth or implant, and on the jawbone itself. Perpendicular occlusal forces of moderate magnitude desirably are broadly distributed over the gum tissue with the attachment simply restricting lateral movement.

The primary object of this invention is to provide an improved attachment for a removable prosthesis that freely yields to perpendicular occlusal forces, ensuring broad distribution to the surrounding gum tissue, and that yields to slight tilting movements all while providing lateral stability. Another object of the present invention is to provide an attachment of this character so designed that the lateral forces are applied to the implant or tooth root at a level very near that of the gum tissue overlying the jawbone crest.

SUMMARY OF INVENTION

In order to accomplish the foregoing objects, I provide a two part attachment in which one part is a pillar attached directly or indirectly to the jawbone, providing an accessible snap-in ball socket. The other part is a ball attached to and projecting from the gum contacting portion of the removable prosthesis or denture. The ball is sized to enter the socket after being forced through its restricted opening. The prosthesis is fitted in such manner that in the absence of occlusal forces, the ball lies at or just inwardly of the restriction. The socket is extended inwardly so that, upon the application of occlusal forces, the ball moves deeper into the socket without imposing stress upon the pillar or its supporting structure. Yet lateral stability is provided. Designed clearance between the neck and the restricted opening allows slight tilting movement of he prosthesis as occlusal forces build.

BRIEF DESCRIPTION OF THE DRAWINGS

A detailed description of the invention will be made with reference to the accompanying drawings wherein like numerals designate corresponding parts in the several figures. Unless described as diagrammatic or unless otherwise indicated, these drawings are to scale.

FIG. 1 is a diagrammatic study corresponding to a commonly used radiographic development of the patient's lower jaw, showing two screw anchors each supporting a pillar providing one part of a two part attachment incorporating the present invention.

FIG. 2 is a diagrammatic longitudinal sectional view of a patient's mouth and illustrating an overdenture in place without occlusal forces.

FIG. 3 is an enlarged axial sectional view of the attachment, including the surrounding bone and gum tissue.

FIG. 4 is a perspective view of the metal screw anchor, which, in the present instance, serves to support one of the attachment parts.

FIG. 5 is a diagrammatic view showing, by the aid of a plastic mouth model, the manner of connection of the overlay denture.

FIG. 6 is an exploded view illustrating the attachment together with a spacer used precisely to position the ball part in the overdenture.

DETAILED DESCRIPTION OF PREFERRED EMBODIMENT

The following detailed description is of the best presently contemplated mode of carrying out the invention. This description is not to be taken in a limiting sense, but is made merely for purposes of illustrating the general principles of the invention, since the scope of the invention is best defined by the appended claims.

In FIG. 1, two identical implants 10 are illustrated that are positioned at, or slightly inside, the cuspid region of the user's lower jaw to be well clear of the nerve canals 12. As shown by the model in FIG. 5, each of the implants 10 carries one part 14 of a snap connector structure. The companion parts 16 are carried by the gum contacting or underside of the overdenture 18.

FIG. 2 illustrates the implant position relative to the patient's mouth. The implant 10 (FIG. 3) comprises a generally cylindrical biocompatible metal screw anchor 20 and a pillar 22 made of plastic or other suitable material. The anchor 20 is installed in a recess prepared in the cancellous bone tissue 26. The recess comprises two parts. The upper part 28 is formed as a simple cylindrical hole of nominal diameter to a depth of seven or eight millimeters beneath the bone crest 30. The lower part 32 of the recess is a deep annular kerf or channel bounded on the inside by a bone core 34 and on the outside by a cylindrical surface of the same diameter as the upper recess part 28.

The anchor 20 fits the prepared recess. The lower part of the anchor 20 is in the form of an inverted hollow core 36 open at its lower end. The core 36 together with a central partition wall 38, caps the bone core 34. The intermediate portion of the anchor 20, just above the partition 38, is provided with three turns of self-tapping threads 40 that engage the wall of the upper recess part 28.

The neck of the anchor projects slightly above the bone crest 30 by an amount less than the thickness of the adjacent gum tissue. A wrench (not shown) fits an hexagonal socket 44 (see also FIG. 4) at the top of the anchor. The manner in which the anchor is trimmed and fitted to the jawbone is described in detail in my U.S. Pat. No. 4,431,416 issued Feb. 14, 1984, and entitled ENDOSSEOUS DENTAL IMPLANT SYSTEM FOR OVERDENTURE RETENTION, CROWN AND BRIDGE SUPPORT.

The attachment comprises a ball 54 (see also FIG. 6) and a snap socket 56. The socket 56 is formed at the head or platform 58 of the pillar 22. The pillar 22 provides a neck 60 just above the top of the anchor 20 (FIG. 3) and about which the gum tissue 42 can grow. The head 58 of the pillar 22 projects only about 3 millimeters above the gum tissue so that lateral force exerted by the ball 54 on the socket 56 acts over a very short lever arm. The small torque is effectively resisted by the anchor.

The ball 54 is formed at the lower end of a connector 62. The connector is attached to a downwardly opening recess 64 of the denture 18. The denture recess 64 surrounds the pillar head 58 with ample clearance to prevent any interaction. The socket 56 has a restricted opening 66 that surrounds the short neck 68 at the base of the ball 54 with a designed clearance of about 0.15 millimeters. The depth of the socket 56 provides a clearance of about 0.50 millimeters or slightly more relative to the ball when the prosthesis is in its nominal position. This ensures that the bite or occlusal force is transmitted via the denture to the gum tissue 42, bypassing or avoiding involvement of the implant in the transmission of such force. Yet the socket 56, together with the socket of the companion implant, provide the requisite lateral stability and retention. Characteristically, the denture slightly tilts from back to front as it settles into position. The designed clearance between the ball neck 68 and the restricted opening 66 allows this movement to take place in a natural unrestricted manner.

In the event that the particular case so permits, the pillar 22 may be attached to a prepared tooth root instead of to an implant.

The connector 62 in the present instance has a series of annular ribs 70 for locking to the denture struture. The connector 62 may be made of plastic such as CELCON ® brand acetal copolymer of the Celanese Corporation or LENNITE brand of ultra high molecular weight polyethylene of Westlake Plastic Company.

The impression of the lower jaw is made with the pillar 22 (FIG. 6) placed in the socket 44 of the anchor 20 or prepared tooth root. A spacer 72 is placed on top of the pillar 22 so that as the impression is made, the ball 54 is at its nominal position at the top of the socket. By the aid of the impression, and in a well understood manner, the lower denture is made with the connectors 62 accurately located.

The pillar 22 is made of stainless steel or suitable alloys providing the requisite characteristics.

The ball 54 and the pillar 22 interact in a manner to dissipate the forces under occlusal function. The flexibility is achieved apart from the metal anchor 20 which is itself rigid and rigidly affixed to the jawbone, or, if used with a prepared tooth root, apart from the tooth root. The flexibility is achieved primarily by the clearance between the parts, and not by the materials of the attachment. The connector 62 is axially short and compact and correspondingly strong, thereby adequately resisting imposed stresses without danger of failure. The lateral contact between the ball 54 and the companion connector part is quite close to the alveolar crest thus to minimize torque on the human and other structures.

Intending to claim all novel, useful and unobvious features shown or described, I make the following claims:

1. A removable dental prosthesis fitted to seat upon the gum tissue of a subject, the combination therewith of:
   (a) a two part attachment for stabilizing said prosthesis in the mouth of the user;
   (b) one of said parts being adapted to be anchored directly or indirectly to the jawbone, said one part providing an accessible snap-in ball socket with a restricted opening;
   (c) the other of said parts being a substantially spherical part or ball adapted to be attached to said prosthesis to project therefrom and to enter said socket;
   (d) said prosthesis having a recess providing clearance entirely about said spherical part or ball;
   (e) said socket being extended inwardly to provide a space for relatively unrestricted longitudinal movement of said spherical part or ball whereby, with said prosthesis fitted so that the ball is nominally located just inwardly of the restriction, perpendicular occlusal forces are sustained primarily by the surrounding gum tissue without contact of said prosthesis recess with said one of said parts.

2. The combination as set forth in claim 1 in which said ball projects from a short neck that has slight clearance with respect to the restricted opening of said socket whereby posterior to anterior tilting movement of the prosthesis is accommodated as occlusal forces are first imposed.

* * * * *